(12) United States Patent
Huang et al.

(10) Patent No.: US 8,775,101 B2
(45) Date of Patent: Jul. 8, 2014

(54) DETECTING DEFECTS ON A WAFER

(75) Inventors: Junqing Huang, Fremont, CA (US);
Yong Zhang, Cupertino, CA (US);
Stephanie Chen, Fremont, CA (US);
Tao Luo, Fremont, CA (US); Lisheng Gao, Morgan Hill, CA (US); Richard Wallingford, San Jose, CA (US)

(73) Assignee: KLA-Tencor Corp., Milpitas, CA (US)

( * ) Notice: Subject to any disclaimer, the term of this patent is extended or adjusted under 35 U.S.C. 154(b) by 338 days.

(21) Appl. No.: 13/196,758

(22) Filed: Aug. 2, 2011

(65) Prior Publication Data

US 2013/0035876 A1    Feb. 7, 2013

Related U.S. Application Data

(63) Continuation of application No. PCT/US2010/023802, filed on Feb. 10, 2010.

(60) Provisional application No. 61/152,477, filed on Feb. 13, 2009.

(51) Int. Cl.
*G01R 31/28* (2006.01)

(52) U.S. Cl.
CPC ..................................... *G01R 31/28* (2013.01)
USPC ............................................................ 702/40

(58) Field of Classification Search
CPC ....................................................... G01R 31/28
USPC ............................................................ 702/40
See application file for complete search history.

(56) References Cited

U.S. PATENT DOCUMENTS

| 3,495,269 | A | 2/1970 | Mutschler et al. |
| 3,496,352 | A | 2/1970 | Jugle |
| 3,909,602 | A | 9/1975 | Micka |
| 4,015,203 | A | 3/1977 | Verkuil |
| 4,247,203 | A | 1/1981 | Levy et al. |
| 4,347,001 | A | 8/1982 | Levy et al. |
| 4,378,159 | A | 3/1983 | Galbraith |
| 4,448,532 | A | 5/1984 | Joseph et al. |
| 4,475,122 | A | 10/1984 | Green |
| 4,532,650 | A | 7/1985 | Wihl et al. |
| 4,555,798 | A | 11/1985 | Broadbent, Jr. et al. |
| 4,578,810 | A | 3/1986 | MacFarlane et al. |
| 4,579,455 | A | 4/1986 | Levy et al. |
| 4,595,289 | A | 6/1986 | Feldman et al. |
| 4,599,558 | A | 7/1986 | Castellano, Jr. et al. |
| 4,633,504 | A | 12/1986 | Wihl |
| 4,641,353 | A | 2/1987 | Kobayashi |

(Continued)

FOREIGN PATENT DOCUMENTS

| CN | 1339140 | 3/2002 |
| CN | 1398348 | 2/2003 |

(Continued)

OTHER PUBLICATIONS

Supplementary European Search Report and European Search Opinion for European Application No. 10 741 683.6 dated Oct. 18, 2012.

(Continued)

*Primary Examiner* — Bryan Bui
(74) *Attorney, Agent, or Firm* — Ann Marie Mewherter

(57) ABSTRACT

Methods and systems for detecting defects on a wafer are provided.

18 Claims, 1 Drawing Sheet

(56) References Cited

U.S. PATENT DOCUMENTS

| | | |
|---|---|---|
| 4,641,967 A | 2/1987 | Pecen |
| 4,734,721 A | 3/1988 | Boyer et al. |
| 4,748,327 A | 5/1988 | Shinozaki et al. |
| 4,758,094 A | 7/1988 | Wihl et al. |
| 4,766,324 A | 8/1988 | Saadat et al. |
| 4,799,175 A | 1/1989 | Sano et al. |
| 4,805,123 A | 2/1989 | Specht et al. |
| 4,812,756 A | 3/1989 | Curtis et al. |
| 4,814,829 A | 3/1989 | Kosugi et al. |
| 4,817,123 A | 3/1989 | Sones et al. |
| 4,845,558 A | 7/1989 | Tsai et al. |
| 4,877,326 A | 10/1989 | Chadwick et al. |
| 4,926,489 A | 5/1990 | Danielson et al. |
| 4,928,313 A | 5/1990 | Leonard et al. |
| 5,046,109 A | 9/1991 | Fujimori et al. |
| 5,124,927 A | 6/1992 | Hopewell et al. |
| 5,189,481 A | 2/1993 | Jann et al. |
| 5,355,212 A | 10/1994 | Wells et al. |
| 5,444,480 A | 8/1995 | Sumita |
| 5,453,844 A | 9/1995 | George et al. |
| 5,481,624 A | 1/1996 | Kamon |
| 5,485,091 A | 1/1996 | Verkuil |
| 5,497,381 A | 3/1996 | O'Donoghue et al. |
| 5,528,153 A | 6/1996 | Taylor et al. |
| 5,544,256 A | 8/1996 | Brecher et al. |
| 5,563,702 A | 10/1996 | Emery et al. |
| 5,572,598 A | 11/1996 | Wihl et al. |
| 5,578,821 A | 11/1996 | Meisberger et al. |
| 5,594,247 A | 1/1997 | Verkuil et al. |
| 5,608,538 A | 3/1997 | Edgar et al. |
| 5,619,548 A | 4/1997 | Koppel |
| 5,621,519 A | 4/1997 | Frost et al. |
| 5,644,223 A | 7/1997 | Verkuil |
| 5,650,731 A | 7/1997 | Fung et al. |
| 5,661,408 A | 8/1997 | Kamieniecki et al. |
| 5,689,614 A | 11/1997 | Gronet et al. |
| 5,694,478 A | 12/1997 | Braier et al. |
| 5,696,835 A | 12/1997 | Hennessey et al. |
| 5,703,969 A | 12/1997 | Hennessey et al. |
| 5,737,072 A | 4/1998 | Emery et al. |
| 5,742,658 A | 4/1998 | Tiffin et al. |
| 5,754,678 A | 5/1998 | Hawthorne et al. |
| 5,767,691 A | 6/1998 | Verkuil |
| 5,767,693 A | 6/1998 | Verkuil |
| 5,771,317 A | 6/1998 | Edgar |
| 5,773,989 A | 6/1998 | Edelman et al. |
| 5,774,179 A | 6/1998 | Chevrette et al. |
| 5,795,685 A | 8/1998 | Liebmann et al. |
| 5,822,218 A | 10/1998 | Moosa et al. |
| 5,831,865 A | 11/1998 | Berezin et al. |
| 5,834,941 A | 11/1998 | Verkuil |
| 5,852,232 A | 12/1998 | Samsavar et al. |
| 5,866,806 A | 2/1999 | Samsavar et al. |
| 5,874,733 A | 2/1999 | Silver et al. |
| 5,884,242 A | 3/1999 | Meier et al. |
| 5,889,593 A | 3/1999 | Bareket |
| 5,917,332 A | 6/1999 | Chen et al. |
| 5,932,377 A | 8/1999 | Ferguson et al. |
| 5,940,458 A | 8/1999 | Suk |
| 5,948,972 A | 9/1999 | Samsavar et al. |
| 5,955,661 A | 9/1999 | Samsavar et al. |
| 5,965,306 A | 10/1999 | Mansfield et al. |
| 5,978,501 A | 11/1999 | Badger et al. |
| 5,980,187 A | 11/1999 | Verhovsky |
| 5,986,263 A | 11/1999 | Hiroi et al. |
| 5,991,699 A | 11/1999 | Kulkarni et al. |
| 5,999,003 A | 12/1999 | Steffan et al. |
| 6,011,404 A | 1/2000 | Ma et al. |
| 6,014,461 A | 1/2000 | Hennessey et al. |
| 6,040,912 A | 3/2000 | Zika et al. |
| 6,052,478 A | 4/2000 | Wihl et al. |
| 6,060,709 A | 5/2000 | Verkuil et al. |
| 6,072,320 A | 6/2000 | Verkuil |
| 6,076,465 A | 6/2000 | Vacca et al. |
| 6,078,738 A | 6/2000 | Garza et al. |
| 6,091,257 A | 7/2000 | Verkuil et al. |
| 6,091,846 A | 7/2000 | Lin et al. |
| 6,097,196 A | 8/2000 | Verkuil et al. |
| 6,097,887 A | 8/2000 | Hardikar et al. |
| 6,104,206 A | 8/2000 | Verkuil |
| 6,104,835 A | 8/2000 | Han |
| 6,117,598 A | 9/2000 | Imai |
| 6,121,783 A | 9/2000 | Horner et al. |
| 6,122,017 A | 9/2000 | Taubman |
| 6,122,046 A | 9/2000 | Almogy |
| 6,137,570 A | 10/2000 | Chuang et al. |
| 6,141,038 A | 10/2000 | Young et al. |
| 6,146,627 A | 11/2000 | Muller et al. |
| 6,171,737 B1 | 1/2001 | Phan et al. |
| 6,175,645 B1 | 1/2001 | Elyasaf et al. |
| 6,184,929 B1 | 2/2001 | Noda et al. |
| 6,184,976 B1 | 2/2001 | Park et al. |
| 6,191,605 B1 | 2/2001 | Miller et al. |
| 6,201,999 B1 | 3/2001 | Jevtic |
| 6,202,029 B1 | 3/2001 | Verkuil et al. |
| 6,205,239 B1 | 3/2001 | Lin et al. |
| 6,215,551 B1 | 4/2001 | Nikoonahad et al. |
| 6,224,638 B1 | 5/2001 | Jevtic et al. |
| 6,233,719 B1 | 5/2001 | Hardikar et al. |
| 6,246,787 B1 | 6/2001 | Hennessey et al. |
| 6,248,485 B1 | 6/2001 | Cuthbert |
| 6,248,486 B1 | 6/2001 | Dirksen et al. |
| 6,259,960 B1 | 7/2001 | Inokuchi |
| 6,266,437 B1 | 7/2001 | Eichel et al. |
| 6,267,005 B1 | 7/2001 | Samsavar et al. |
| 6,268,093 B1 | 7/2001 | Kenan et al. |
| 6,272,236 B1 | 8/2001 | Pierrat et al. |
| 6,282,309 B1 | 8/2001 | Emery |
| 6,292,582 B1 | 9/2001 | Lin et al. |
| 6,324,298 B1 | 11/2001 | O'Dell et al. |
| 6,344,640 B1 | 2/2002 | Rhoads |
| 6,363,166 B1 | 3/2002 | Wihl et al. |
| 6,373,975 B1 | 4/2002 | Bula et al. |
| 6,388,747 B2 | 5/2002 | Nara et al. |
| 6,393,602 B1 | 5/2002 | Atchison et al. |
| 6,407,373 B1 | 6/2002 | Dotan |
| 6,415,421 B2 | 7/2002 | Anderson et al. |
| 6,445,199 B1 | 9/2002 | Satya et al. |
| 6,451,690 B1 | 9/2002 | Matsumoto et al. |
| 6,459,520 B1 | 10/2002 | Takayama |
| 6,466,314 B1 | 10/2002 | Lehman |
| 6,466,315 B1 | 10/2002 | Karpol et al. |
| 6,470,489 B1 | 10/2002 | Chang et al. |
| 6,483,938 B1 | 11/2002 | Hennessey et al. |
| 6,513,151 B1 | 1/2003 | Erhardt et al. |
| 6,526,164 B1 | 2/2003 | Mansfield et al. |
| 6,529,621 B1 | 3/2003 | Glasser et al. |
| 6,535,628 B2 | 3/2003 | Smargiassi et al. |
| 6,539,106 B1 | 3/2003 | Gallarda et al. |
| 6,569,691 B1 | 5/2003 | Jastrzebski et al. |
| 6,581,193 B1 | 6/2003 | McGhee et al. |
| 6,593,748 B1 | 7/2003 | Halliyal et al. |
| 6,597,193 B2 | 7/2003 | Lagowski et al. |
| 6,602,728 B1 | 8/2003 | Liebmann et al. |
| 6,608,681 B2 | 8/2003 | Tanaka et al. |
| 6,614,520 B1 | 9/2003 | Bareket et al. |
| 6,631,511 B2 | 10/2003 | Haffner et al. |
| 6,636,301 B1 | 10/2003 | Kvamme et al. |
| 6,642,066 B1 | 11/2003 | Halliyal et al. |
| 6,658,640 B2 | 12/2003 | Weed |
| 6,665,065 B1 | 12/2003 | Phan et al. |
| 6,670,082 B2 | 12/2003 | Liu et al. |
| 6,680,621 B2 | 1/2004 | Savtchouk |
| 6,691,052 B1 | 2/2004 | Maurer |
| 6,701,004 B1 | 3/2004 | Shykind et al. |
| 6,718,526 B1 | 4/2004 | Eldredge et al. |
| 6,721,695 B1 | 4/2004 | Chen et al. |
| 6,734,696 B2 | 5/2004 | Horner et al. |
| 6,738,954 B1 | 5/2004 | Allen et al. |
| 6,748,103 B2 | 6/2004 | Glasser et al. |
| 6,751,519 B1 | 6/2004 | Satya et al. |
| 6,753,954 B2 | 6/2004 | Chen |
| 6,757,645 B2 | 6/2004 | Chang et al. |
| 6,759,655 B2 | 7/2004 | Nara et al. |

(56) References Cited

U.S. PATENT DOCUMENTS

| | | |
|---|---|---|
| 6,771,806 B1 | 8/2004 | Satya et al. |
| 6,775,818 B2 | 8/2004 | Taravade et al. |
| 6,777,147 B1 | 8/2004 | Fonseca et al. |
| 6,777,676 B1 | 8/2004 | Wang et al. |
| 6,778,695 B1 | 8/2004 | Schellenberg et al. |
| 6,779,159 B2 | 8/2004 | Yokoyama et al. |
| 6,784,446 B1 | 8/2004 | Phan et al. |
| 6,788,400 B2 | 9/2004 | Chen |
| 6,789,032 B2 | 9/2004 | Barbour et al. |
| 6,803,554 B2 | 10/2004 | Ye et al. |
| 6,806,456 B1 | 10/2004 | Ye et al. |
| 6,807,503 B2 | 10/2004 | Ye et al. |
| 6,813,572 B2 | 11/2004 | Satya et al. |
| 6,820,028 B2 | 11/2004 | Ye et al. |
| 6,828,542 B2 | 12/2004 | Ye et al. |
| 6,842,225 B1 | 1/2005 | Irie |
| 6,859,746 B1 | 2/2005 | Stirton |
| 6,879,403 B2 | 4/2005 | Freifeld |
| 6,879,924 B2 | 4/2005 | Ye et al. |
| 6,882,745 B2 | 4/2005 | Brankner et al. |
| 6,884,984 B2 | 4/2005 | Ye et al. |
| 6,886,153 B1 | 4/2005 | Bevis |
| 6,892,156 B2 | 5/2005 | Ye et al. |
| 6,902,855 B2 | 6/2005 | Peterson et al. |
| 6,906,305 B2 | 6/2005 | Pease et al. |
| 6,918,101 B1 | 7/2005 | Satya et al. |
| 6,919,957 B2 | 7/2005 | Nikoonahad et al. |
| 6,937,753 B1 | 8/2005 | O'Dell et al. |
| 6,948,141 B1 | 9/2005 | Satya et al. |
| 6,959,255 B2 | 10/2005 | Ye et al. |
| 6,966,047 B1 | 11/2005 | Glasser |
| 6,969,837 B2 | 11/2005 | Ye et al. |
| 6,969,864 B2 | 11/2005 | Ye et al. |
| 6,983,060 B1 | 1/2006 | Martinent-Catalot et al. |
| 6,988,045 B2 | 1/2006 | Purdy |
| 7,003,755 B2 | 2/2006 | Pang et al. |
| 7,003,758 B2 | 2/2006 | Ye et al. |
| 7,012,438 B1 | 3/2006 | Miller et al. |
| 7,026,615 B2 | 4/2006 | Takane et al. |
| 7,027,143 B1 | 4/2006 | Stokowski et al. |
| 7,030,966 B2 | 4/2006 | Hansen |
| 7,030,997 B2 | 4/2006 | Neureuther et al. |
| 7,053,355 B2 | 5/2006 | Ye et al. |
| 7,061,625 B1 | 6/2006 | Hwang et al. |
| 7,071,833 B2 | 7/2006 | Nagano et al. |
| 7,103,484 B1 | 9/2006 | Shi et al. |
| 7,106,895 B1 | 9/2006 | Goldberg et al. |
| 7,107,517 B1 | 9/2006 | Suzuki et al. |
| 7,107,571 B2 | 9/2006 | Chang et al. |
| 7,111,277 B2 | 9/2006 | Ye et al. |
| 7,114,143 B2 | 9/2006 | Hanson et al. |
| 7,114,145 B2 | 9/2006 | Ye et al. |
| 7,117,477 B2 | 10/2006 | Ye et al. |
| 7,117,478 B2 | 10/2006 | Ye et al. |
| 7,120,285 B1 | 10/2006 | Spence |
| 7,120,895 B2 | 10/2006 | Ye et al. |
| 7,123,356 B1 | 10/2006 | Stokowski et al. |
| 7,124,386 B2 | 10/2006 | Smith et al. |
| 7,133,548 B2 | 11/2006 | Kenan et al. |
| 7,135,344 B2 | 11/2006 | Nehmadi et al. |
| 7,136,143 B2 | 11/2006 | Smith |
| 7,152,215 B2 | 12/2006 | Smith et al. |
| 7,162,071 B2 | 1/2007 | Hung et al. |
| 7,171,334 B2 | 1/2007 | Gassner |
| 7,174,520 B2 | 2/2007 | White et al. |
| 7,194,709 B2 | 3/2007 | Brankner |
| 7,207,017 B1 | 4/2007 | Tabery et al. |
| 7,231,628 B2 | 6/2007 | Pack et al. |
| 7,236,847 B2 | 6/2007 | Marella |
| 7,271,891 B1 | 9/2007 | Xiong et al. |
| 7,379,175 B1 | 5/2008 | Stokowski et al. |
| 7,383,156 B2 | 6/2008 | Matsusita et al. |
| 7,386,839 B1 | 6/2008 | Golender et al. |
| 7,388,979 B2 | 6/2008 | Sakai et al. |
| 7,418,124 B2 | 8/2008 | Peterson et al. |
| 7,424,145 B2 | 9/2008 | Horie et al. |
| 7,440,093 B1 | 10/2008 | Xiong et al. |
| 7,570,796 B2 | 8/2009 | Zafar et al. |
| 7,676,077 B2 | 3/2010 | Kulkarni et al. |
| 7,683,319 B2 | 3/2010 | Makino et al. |
| 7,738,093 B2 | 6/2010 | Alles et al. |
| 7,739,064 B1 | 6/2010 | Ryker et al. |
| 7,760,929 B2 | 7/2010 | Orbon et al. |
| 7,877,722 B2 | 1/2011 | Duffy et al. |
| 7,890,917 B1 | 2/2011 | Young et al. |
| 7,904,845 B2 | 3/2011 | Fouquet et al. |
| 7,968,859 B2 | 6/2011 | Young et al. |
| 8,073,240 B2 | 12/2011 | Fischer et al. |
| 8,126,255 B2 | 2/2012 | Bhaskar et al. |
| 2001/0017694 A1 | 8/2001 | Oomori et al. |
| 2001/0019625 A1 | 9/2001 | Kenan et al. |
| 2001/0022858 A1 | 9/2001 | Komiya et al. |
| 2001/0043735 A1 | 11/2001 | Smargiassi et al. |
| 2002/0010560 A1 | 1/2002 | Balachandran |
| 2002/0019729 A1 | 2/2002 | Chang et al. |
| 2002/0026626 A1 | 2/2002 | Randall et al. |
| 2002/0033449 A1 | 3/2002 | Nakasuji et al. |
| 2002/0035461 A1 | 3/2002 | Chang et al. |
| 2002/0035641 A1 | 3/2002 | Kurose et al. |
| 2002/0035717 A1 | 3/2002 | Matsuoka |
| 2002/0088951 A1 | 7/2002 | Chen |
| 2002/0090746 A1 | 7/2002 | Xu et al. |
| 2002/0134936 A1 | 9/2002 | Matsui et al. |
| 2002/0144230 A1 | 10/2002 | Rittman |
| 2002/0145734 A1 | 10/2002 | Watkins et al. |
| 2002/0164065 A1 | 11/2002 | Cai et al. |
| 2002/0176096 A1 | 11/2002 | Sentoku et al. |
| 2002/0181756 A1 | 12/2002 | Shibuya et al. |
| 2002/0186878 A1 | 12/2002 | Hoon et al. |
| 2002/0192578 A1 | 12/2002 | Tanaka et al. |
| 2003/0004699 A1 | 1/2003 | Choi et al. |
| 2003/0014146 A1 | 1/2003 | Fujii et al. |
| 2003/0017664 A1 | 1/2003 | Pnueli et al. |
| 2003/0022401 A1 | 1/2003 | Hamamatsu et al. |
| 2003/0033046 A1 | 2/2003 | Yoshitake et al. |
| 2003/0048458 A1 | 3/2003 | Mieher et al. |
| 2003/0048939 A1 | 3/2003 | Lehman |
| 2003/0057971 A1 | 3/2003 | Nishiyama et al. |
| 2003/0076989 A1 | 4/2003 | Maayah et al. |
| 2003/0086081 A1 | 5/2003 | Lehman |
| 2003/0094572 A1 | 5/2003 | Matsui et al. |
| 2003/0098805 A1 | 5/2003 | Bizjak et al. |
| 2003/0128870 A1 | 7/2003 | Pease et al. |
| 2003/0138138 A1 | 7/2003 | Vacca et al. |
| 2003/0138978 A1 | 7/2003 | Tanaka et al. |
| 2003/0169916 A1 | 9/2003 | Hayashi et al. |
| 2003/0173516 A1 | 9/2003 | Takane et al. |
| 2003/0192015 A1 | 10/2003 | Liu |
| 2003/0207475 A1 | 11/2003 | Nakasuji et al. |
| 2003/0223639 A1 | 12/2003 | Shlain et al. |
| 2003/0226951 A1 | 12/2003 | Ye et al. |
| 2003/0227620 A1 | 12/2003 | Yokoyama et al. |
| 2003/0228714 A1 | 12/2003 | Smith et al. |
| 2003/0229410 A1 | 12/2003 | Smith et al. |
| 2003/0229412 A1 | 12/2003 | White et al. |
| 2003/0229868 A1 | 12/2003 | White et al. |
| 2003/0229875 A1 | 12/2003 | Smith et al. |
| 2003/0229880 A1 | 12/2003 | White et al. |
| 2003/0229881 A1 | 12/2003 | White et al. |
| 2003/0237064 A1 | 12/2003 | White et al. |
| 2004/0030430 A1 | 2/2004 | Matsuoka |
| 2004/0032908 A1 | 2/2004 | Hagai et al. |
| 2004/0049722 A1 | 3/2004 | Matsushita |
| 2004/0052411 A1 | 3/2004 | Qian et al. |
| 2004/0057611 A1 | 3/2004 | Lee et al. |
| 2004/0066506 A1 | 4/2004 | Elichai et al. |
| 2004/0091142 A1 | 5/2004 | Peterson et al. |
| 2004/0094762 A1 | 5/2004 | Hess et al. |
| 2004/0098216 A1 | 5/2004 | Ye et al. |
| 2004/0102934 A1 | 5/2004 | Chang |
| 2004/0107412 A1 | 6/2004 | Pack et al. |
| 2004/0119036 A1 | 6/2004 | Ye et al. |
| 2004/0120569 A1 | 6/2004 | Hung et al. |
| 2004/0133369 A1 | 7/2004 | Pack et al. |

(56) References Cited

U.S. PATENT DOCUMENTS

| | | |
|---|---|---|
| 2004/0147121 A1 | 7/2004 | Nakagaki et al. |
| 2004/0174506 A1 | 9/2004 | Smith |
| 2004/0179738 A1 | 9/2004 | Dai et al. |
| 2004/0199885 A1 | 10/2004 | Lu et al. |
| 2004/0223639 A1 | 11/2004 | Sato et al. |
| 2004/0228515 A1 | 11/2004 | Okabe et al. |
| 2004/0234120 A1 | 11/2004 | Honda et al. |
| 2004/0243320 A1 | 12/2004 | Chang et al. |
| 2004/0246476 A1 | 12/2004 | Bevis et al. |
| 2004/0254752 A1 | 12/2004 | Wisniewski et al. |
| 2005/0004774 A1 | 1/2005 | Volk et al. |
| 2005/0008218 A1 | 1/2005 | O'Dell et al. |
| 2005/0010890 A1 | 1/2005 | Nehmadi et al. |
| 2005/0013474 A1 | 1/2005 | Sim |
| 2005/0062962 A1 | 3/2005 | Fairley et al. |
| 2005/0069217 A1 | 3/2005 | Mukherjee |
| 2005/0117796 A1 | 6/2005 | Matsui et al. |
| 2005/0132306 A1 | 6/2005 | Smith et al. |
| 2005/0141764 A1 | 6/2005 | Tohyama et al. |
| 2005/0166174 A1 | 7/2005 | Ye et al. |
| 2005/0184252 A1 | 8/2005 | Ogawa et al. |
| 2005/0190957 A1 | 9/2005 | Cai et al. |
| 2005/0198602 A1 | 9/2005 | Brankner et al. |
| 2006/0000964 A1 | 1/2006 | Ye et al. |
| 2006/0036979 A1 | 2/2006 | Zurbrick et al. |
| 2006/0038986 A1 | 2/2006 | Honda et al. |
| 2006/0048089 A1 | 3/2006 | Schwarzband |
| 2006/0051682 A1 | 3/2006 | Hess et al. |
| 2006/0062445 A1 | 3/2006 | Verma et al. |
| 2006/0066339 A1 | 3/2006 | Rajski et al. |
| 2006/0082763 A1 | 4/2006 | Teh et al. |
| 2006/0159333 A1 | 7/2006 | Ishikawa |
| 2006/0161452 A1 | 7/2006 | Hess |
| 2006/0193506 A1 | 8/2006 | Dorphan et al. |
| 2006/0193507 A1 | 8/2006 | Sali et al. |
| 2006/0236294 A1 | 10/2006 | Saidin et al. |
| 2006/0236297 A1 | 10/2006 | Melvin, III et al. |
| 2006/0239536 A1 | 10/2006 | Shibuya et al. |
| 2006/0265145 A1 | 11/2006 | Huet et al. |
| 2006/0266243 A1 | 11/2006 | Percin et al. |
| 2006/0269120 A1 | 11/2006 | Nehmadi et al. |
| 2006/0273242 A1 | 12/2006 | Hunsche et al. |
| 2006/0273266 A1 | 12/2006 | Preil et al. |
| 2006/0277520 A1 | 12/2006 | Gennari |
| 2006/0291714 A1 | 12/2006 | Wu et al. |
| 2006/0292463 A1 | 12/2006 | Best et al. |
| 2007/0002322 A1 | 1/2007 | Borodovsky et al. |
| 2007/0011628 A1 | 1/2007 | Ouali et al. |
| 2007/0013901 A1 | 1/2007 | Kim et al. |
| 2007/0019171 A1 | 1/2007 | Smith |
| 2007/0019856 A1 | 1/2007 | Furman et al. |
| 2007/0031745 A1 | 2/2007 | Ye et al. |
| 2007/0032896 A1 | 2/2007 | Ye et al. |
| 2007/0035322 A1 | 2/2007 | Kang et al. |
| 2007/0035712 A1 | 2/2007 | Gassner et al. |
| 2007/0035728 A1 | 2/2007 | Kekare et al. |
| 2007/0052963 A1 | 3/2007 | Orbon et al. |
| 2007/0064995 A1 | 3/2007 | Oaki et al. |
| 2007/0133860 A1 | 6/2007 | Lin et al. |
| 2007/0156379 A1 | 7/2007 | Kulkarni et al. |
| 2007/0230770 A1 | 10/2007 | Kulkarni et al. |
| 2007/0248257 A1 | 10/2007 | Bruce et al. |
| 2007/0280527 A1 | 12/2007 | Almogy et al. |
| 2007/0288219 A1 | 12/2007 | Zafar et al. |
| 2008/0013083 A1 | 1/2008 | Kirk et al. |
| 2008/0049994 A1 | 2/2008 | Rognin et al. |
| 2008/0058977 A1 | 3/2008 | Honda |
| 2008/0072207 A1 | 3/2008 | Verma et al. |
| 2008/0081385 A1 | 4/2008 | Marella et al. |
| 2008/0163140 A1 | 7/2008 | Fouquet et al. |
| 2008/0167829 A1 | 7/2008 | Park et al. |
| 2008/0250384 A1 | 10/2008 | Duffy et al. |
| 2008/0295047 A1 | 11/2008 | Nehmadi et al. |
| 2008/0295048 A1 | 11/2008 | Nehmadi et al. |
| 2008/0304056 A1 | 12/2008 | Alles et al. |
| 2009/0024967 A1 | 1/2009 | Su et al. |
| 2009/0037134 A1 | 2/2009 | Kulkarni et al. |
| 2009/0041332 A1 | 2/2009 | Bhaskar et al. |
| 2009/0043527 A1 | 2/2009 | Park et al. |
| 2009/0055783 A1 | 2/2009 | Florence et al. |
| 2009/0080759 A1 | 3/2009 | Bhaskar et al. |
| 2009/0210183 A1 | 8/2009 | Rajski et al. |
| 2009/0257645 A1 | 10/2009 | Chen et al. |
| 2009/0284733 A1* | 11/2009 | Wallingford et al. ........... 356/73 |
| 2009/0290782 A1 | 11/2009 | Regensburger |
| 2010/0142800 A1 | 6/2010 | Pak et al. |
| 2010/0146338 A1 | 6/2010 | Schalick et al. |
| 2010/0150429 A1 | 6/2010 | Jau et al. |
| 2011/0052040 A1 | 3/2011 | Kuan |
| 2011/0184662 A1 | 7/2011 | Badger et al. |
| 2012/0319246 A1 | 12/2012 | Tan et al. |
| 2013/0009989 A1 | 1/2013 | Chen et al. |
| 2013/0027196 A1 | 1/2013 | Yankun et al. |

FOREIGN PATENT DOCUMENTS

| | | |
|---|---|---|
| CN | 1646896 | 7/2005 |
| EP | 0032197 | 7/1981 |
| EP | 0370322 | 5/1990 |
| EP | 1061358 | 12/2000 |
| EP | 1061571 | 12/2000 |
| EP | 1065567 | 1/2001 |
| EP | 1066925 | 1/2001 |
| EP | 1069609 | 1/2001 |
| EP | 1093017 | 4/2001 |
| EP | 1329771 | 7/2003 |
| EP | 1480034 | 11/2004 |
| EP | 1696270 | 8/2006 |
| JP | 7-159337 | 6/1995 |
| JP | 2002071575 | 3/2002 |
| JP | 2002365235 | 12/2002 |
| JP | 2003-215060 | 7/2003 |
| JP | 2004045066 | 2/2004 |
| JP | 2005-283326 | 10/2005 |
| JP | 2009-122046 | 6/2009 |
| KR | 10-2001-0007394 | 1/2001 |
| KR | 10-2001-0037206 | 5/2001 |
| KR | 10-2001-0101697 | 11/2001 |
| KR | 1020030055848 | 7/2003 |
| KR | 1020050092053 | 9/2005 |
| KR | 10-2006-0075691 | 7/2006 |
| KR | 10-2010-0061018 | 6/2010 |
| WO | 9857358 | 12/1998 |
| WO | 9922310 | 5/1999 |
| WO | 9925004 | 5/1999 |
| WO | 9959200 | 5/1999 |
| WO | 9938002 | 7/1999 |
| WO | 9941434 | 8/1999 |
| WO | 0003234 | 1/2000 |
| WO | 0036525 | 6/2000 |
| WO | 0055799 | 9/2000 |
| WO | 0068884 | 11/2000 |
| WO | 0070332 | 11/2000 |
| WO | 0109566 | 2/2001 |
| WO | 0140145 | 6/2001 |
| WO | 03104921 | 12/2003 |
| WO | 2004027684 | 4/2004 |
| WO | 2006063268 | 6/2006 |
| WO | 2010/093733 | 8/2010 |

OTHER PUBLICATIONS

Huang et al., "Using Design Based Binning to Improve Defect Excursion Control for 45nm Production," IEEE, International Symposium on Semiconductor Manufacturing, Oct. 2007, pp. 1-3.

International Preliminary Report on Patentability for PCT/US2010/023802 mailed Aug. 25, 2011.

Sato et al., "Defect Criticality Index (DCI): A new methodology to significantly improve DOI sampling rate in a 45nm production environment," Metrology, Inspection, and Process Control for Microlithography XXII, Proc. Of SPIE vol. 6922, 692213 (2008), pp. 1-9.

U.S. Appl. No. 60/418,994, filed Oct. 15, 2002 by Stokowski et al.

(56) References Cited

OTHER PUBLICATIONS

U.S. Appl. No. 60/419,028, filed Oct. 15, 2002 by Stokowski et al.
U.S. Appl. No. 60/451,707, filed Mar. 4, 2003 by Howard et al.
U.S. Appl. No. 60/485,233, filed Jul. 7, 2003 by Peterson et al.
U.S. Appl. No. 60/526,881, filed Dec. 4, 2003 by Hess et al.
U.S. Appl. No. 60/609,670, filed Sep. 14, 2004 by Preil et al.
U.S. Appl. No. 60/681,095, filed May 13, 2005 by Nehmadi et al.
U.S. Appl. No. 60/684,360, filed May 24, 2005 by Nehmadi et al.
U.S. Appl. No. 60/738,290, filed Nov. 18, 2005 by Kulkarni et al.
U.S. Appl. No. 60/772,418, filed Feb. 9, 2006 by Kirk et al.
U.S. Appl. No. 10/778,752, filed Feb. 13, 2004 by Preil et al.
U.S. Appl. No. 10/793,599, filed Mar. 4, 2004 by Howard et al.
U.S. Appl. No. 11/139,151, filed Feb. 10, 2005 by Volk.
U.S. Appl. No. 11/154,310, filed Feb. 10, 2005 by Verma et al.
U.S. Appl. No. 12/102,343, filed Apr. 14, 2008 by Chen et al.
U.S. Appl. No. 12/394,752, filed Feb. 27, 2009 by Xiong et al.
U.S. Appl. No. 12/403,905, filed Mar. 13, 2009 by Xiong.
Allan et al., "Critical Area Extraction for Soft Fault Estimation," IEEE Transactions on Semiconductor Manufacturing, vol. 11, No. 1, Feb. 1998.
Barty et al., "Aerial Image Microscopes for the inspection of defects in EUV masks," Proceedings of SPIE, vol. 4889, 2002, pp. 1073-1084.
Budd et al., "A New Mask Evaluation Tool, the Microlithography Simulation Microscope Aerial Image Measurement System," SPIE vol. 2197, 1994, pp. 530-540.
Cai et al., "Enhanced Dispositioning of Reticle Defects Using the Virtual Stepper With Automated Defect Severity Scoring," Proceedings of the SPIE, vol. 4409, Jan. 2001, pp. 467-478.
Comizzoli, "Uses of Corona Discharges in the Semiconductor Industry," J. Electrochem. Soc., 1987, pp. 424-429.
Contactless Electrical Equivalent Oxide Thickness Measurement, IBM Technical Disclosure Bulletin, vol. 29, No. 10, 1987, pp. 4622-4623.
Contactless Photovoltage vs. Bias Method for Determining Flat-Band Voltage, IBM Technical Disclosure Bulletin, vol. 32, vol. 9A, 1990, pp. 14-17.
Cosway et al., "Manufacturing Implementation of Corona Oxide Silicon (COS) Systems for Diffusion Furnace Contamination Monitoring," 1997 IEEE/SEMI Advanced Semiconductor Manufacturing Conference, pp. 98-102.
Diebold et al., "Characterization and production metrology of thin transistor gate oxide films," Materials Science in Semiconductor Processing 2, 1999, pp. 103-147.
Dirksen et al., "Impact of high order aberrations on the performance of the aberration monitor," Proc. Of SPIE vol. 4000, Mar. 2000, pp. 9-17.
Dirksen et al., "Novel aberration monitor for optical lithography," Proc. Of SPIE vol. 3679, Jul. 1999, pp. 77-86.
Garcia et al., "New Die to Database Inspection Algorithm for Inspection of 90-nm Node Reticles," Proceedings of SPIE, vol. 5130, 2003, pp. 364-374.
Granik et al., "Sub-resolution process windows and yield estimation technique based on detailed full-chip CD simulation," Mentor Graphics, Sep. 2000, 5 pages.
Hess et al., "A Novel Approach: High Resolution Inspection with Wafer Plane Defect Detection," Proceedings of SPIE—International Society for Optical Engineering; Photomask and Next-Generation Lithography Mask Technology 2008, vol. 7028, 2008.
Huang et al., "Process Window Impact of Progressive Mask Defects, Its Inspection and Disposition Techniques (go/no-go criteria) Via a Lithographic Detector," Proceedings of SPIE—The International Society for Optical Engineering; 25th Annual Bacus Symposium on Photomask Technology 2005, vol. 5992, No. 1, 2005, p. 6.
Hung et al., Metrology Study of Sub 20 Angstrom oxynitride by Corona-Oxide-Silicon (COS) and Conventional C-V Approaches, 2002, Mat. Res. Soc. Symp. Proc., vol. 716, pp. 119-124.
International Search Report for PCT/US2003/021907 mailed Jun. 7, 2004.
International Search Report for PCT/US2004/040733 mailed Dec. 23, 2005.
International Search Report for PCT/US2006/061112 mailed Sep. 25, 2008.
International Search Report for PCT/US2006/061113 mailed Jul. 16, 2008.
International Search Report for PCT/US2008/050397 mailed Jul. 11, 2008.
International Search Report for PCT/US2008/062873 mailed Aug. 12, 2008.
International Search Report for PCT/US2008/062875 mailed Sep. 10, 2008.
International Search Report for PCT/US2008/063008 mailed Aug. 18, 2008.
International Search Report for PCT/US2008/066328 mailed Oct. 1, 2009.
International Search Report for PCT/US2008/070647 mailed Dec. 16, 2008.
International Search Report for PCT/US2008/072636 mailed Jan. 29, 2009.
International Search Report for PCT/US2008/073706 mailed Jan. 29, 2009.
International Search Report for PCT/US2009/051961 mailed Mar. 16, 2010.
Karklin et al., "Automatic Defect Severity Scoring for 193 nm Reticle Defect Inspection," Proceedings of SPIE—The International Society for Optical Engineering, 2001, vol. 4346, No. 2, pp. 898-906.
Lo et al., "Identifying Process Window Marginalities of Reticle Designs for 0.15/0.13 µm Technologies," Proceedings of SPIE vol. 5130, 2003, pp. 829-837.
Lorusso et al. "Advanced DFM Applns. Using design-based metrology on CDSEM," SPIE vol. 6152, Mar. 27, 2006.
Lu et al., "Application of Simulation Based Defect Printability Analysis for Mask Qualification Control," Proceedings of SPIE, vol. 5038, 2003, pp. 33-40.
Mack, "Lithographic Simulation: A Review," Proceedings of SPIE vol. 4440, 2001, pp. 59-72.
Martino et al., "Application of the Aerial Image Measurement System (AIMS(TM)) to the Analysis of Binary Mask Imaging and Resolution Enhancement Techniques," SPIE vol. 2197, 1994, pp. 573-584.
Miller, "A New Approach for Measuring Oxide Thickness," Semiconductor International, Jul. 1995, pp. 147-148.
Nagpal et al., "Wafer Plane Inspection for Advanced Reticle Defects," Proceedings of SPIE—The International Society for Optical Engineering; Photomask and Next-Generation Lithography Mask Technology. vol. 7028, 2008.
Numerical Recipes in C. The Art of Scientific Computing, 2nd Ed.,© Cambridge University Press 1988, 1992, p. 683.
O'Gorman et al., "Subpixel Registration Using a Concentric Ring Fiducial," Proceedings of the International Conference on Pattern Recognition, vol. ii, Jun. 16, 1990, pp. 249-253.
Otsu, "A Threshold Selection Method from Gray-Level Histograms," IEEE Transactions on Systems, Man, and Cybernetics, vol. SMC-9, No. 1, Jan. 1979, pp. 62-66.
Pang et al., "Simulation-based Defect Printability Analysis on Alternating Phase Shifting Masks for 193 nm Lithography," Proceedings of SPIE, vol. 4889, 2002, pp. 947-954.
Pettibone et al., "Wafer Printability Simulation Accuracy Based on UV Optical Inspection Images of Reticle Defects," Proceedings of SPIE—The International Society for Optical Engineering 1999 Society of Photo-Optical Instrumentation Engineers, vol. 3677, No. II, 1999, pp. 711-720.
Phan et al., "Comparison of Binary Mask Defect Printability Analysis Using Virtual Stepper System and Aerial Image Microscope System," Proceedings of SPIE—The International Society for Optical Engineering 1999 Society of Photo-Optical Instrumentation Engineers, vol. 3873, 1999, pp. 681-692.
Sahouria et al., "Full-chip Process Simulation for Silicon DRC," Mentor Graphics, Mar. 2000, 6 pages.
Schroder et al., Corona-Oxide-Semiconductor Device Characterization, 1998, Solid-State Electronics, vol. 42, No. 4, pp. 505-512.

(56) References Cited

OTHER PUBLICATIONS

Schroder, "Surface voltage and surface photovoltage: history, theory and applications," Measurement Science and Technology, vol. 12, 2001, pp. R16-R31.

Schroder, Contactless Surface Charge Semiconductor Characterization, Apr. 2002, Materials Science and Engineering B, vol. 91-92, pp. 196-228.

Schurz et al., "Simulation Study of Reticle Enhancement Technology Applications for 157 nm Lithography," SPIE vol. 4562, 2002, pp. 902-913.

Svidenko et al. "Dynamic Defect-Limited Yield Prediction by Criticality Factor," ISSM Paper: YE-O-157, 2007.

Tang et al., "Analyzing Volume Diagnosis Results with Statistical Learning for Yield Improvement" 12th IEEE European Test Symposium, Freiburg 2007, IEEE European, May 20-24, 2007, pp. 145-150.

Verkuil et al., "A Contactless Alternative to MOS Charge Measurements by Means of a Corona-Oxide-Semiconductor (COS) Technique,"Electrochem. Soc. Extended Abstracts, 1988, vol. 88-1, No. 169, pp. 261-262.

Verkuil, "Rapid Contactless Method for Measuring Fixed Oxide Charge Associated with Silicon Processing," IBM Technical Disclosure Bulletin, vol. 24, No. 6, 1981, pp. 3048-3053.

Volk et al. "Investigation of Reticle Defect Formation at DUV Lithography," 2002, BACUS Symposium on Photomask Technology.

Volk et al. "Investigation of Reticle Defect Formation at DUV Lithography," 2003, IEEE/SEMI Advanced Manufacturing Conference, pp. 29-35.

Volk et al., "Investigation of Smart Inspection of Critical Layer Reticles using Additional Designer Data to Determine Defect Significance," Proceedings of SPIE vol. 5256, 2003, pp. 489-499.

Weinberg, "Tunneling of Electrons from Si into Thermally Grown $SiO_2$," Solid-State Electronics, 1977, vol. 20, pp. 11-18.

Weinzierl et al., "Non-Contact Corona-Based Process Control Measurements: Where We've Been, Where We're Headed," Electrochemical Society Proceedings, Oct. 1999, vol. 99-16, pp. 342-350.

Yan et al., "Printability of Pellicle Defects in DUV 0.5 um Lithography," SPIE vol. 1604, 1991, pp. 106-117.

International Search Report and Written Opinion for PCT/US2010/023802 mailed Aug. 30, 2010.

Office Action for Chinese Patent Application No. 201080016422.8 mailed Sep. 30, 2013, No English.

Office Action for Japanese Patent Application 2011-550208 mailed on Nov. 5, 2013, No English.

U.S. Appl. No. 13/652,377, filed Oct. 15, 2012 by Wu et al.

Guo et al., "License Plate Localization and Character Segmentation with Feedback Self-Learning and Hybrid Binarization Techniques," IEEE Transactions on Vehicular Technology, vol. 57, No. 3, May 2008, pp. 1417-1424.

Liu, "Robust Image Segmentation Using Local Median," Proceedings of the 3rd Canadian Conference on Computer and Robot Vision (CRV'06) 0-7695-2542-Mar. 6, 2006 IEEE, 7 pages total.

\* cited by examiner

DETECTING DEFECTS ON A WAFER

CROSS-REFERENCE TO RELATED APPLICATIONS

This application is a continuation. of International Application No. PCT/US10/23802 filed Feb. 10, 2010, which application claims priority to U.S. Provisional Application No. 61/152,477 entitled "Methods and Systems for Detecting Defects on a Wafer," filed Feb 13, 2009, which is incorporated by reference as if fully set forth herein.

BACKGROUND OF THE INVENTION

1. Field of the Invention

This invention generally relates to detecting defects on a wafer. Certain embodiments relate to assigning individual output in raw output for a wafer generated by an inspection system to different segments.

2. Description of the Related Art

The following description and examples are not admitted to be prior art by virtue of their inclusion in this section.

Wafer inspection, using either optical or electron beam technologies, is an important technique for debugging semiconductor manufacturing processes, monitoring process variations, and improving production yield in the semiconductor industry. With the ever decreasing scale of modern integrated circuits (ICs) as well as the increasing complexity of the manufacturing process, inspection becomes more and more difficult.

In each processing step performed on a semiconductor wafer, the same circuit pattern is printed in each die on the wafer. Most wafer inspection systems take advantage of this fact and use a relatively simple die-to-die comparison to detect defects on the wafer. However, the printed circuit in each die may include many areas of patterned features that repeat in the x or y direction such as the areas of DRAM, SRAM, or FLASH. This type of area is commonly referred to as an array area (the rest of the areas are called random or logic areas). To achieve better sensitivity, advanced inspection systems employ different strategies for inspecting the array areas and the random or logic areas.

To set up a wafer inspection process for array inspection, many currently used inspection systems require users to manually set up regions of interest (ROI) and apply the same set of parameters for defect detection in the same ROI. However, this method of set up is disadvantageous for a number of reasons. For example, as design rules shrink, region definition can be much more complicated and much smaller in area. With the limitations on stage accuracy and resolution of the inspection system, manual set up of ROI will become impossible eventually. On the other hand, if the distance between page breaks is larger than Fourier filtering can perform, the page break will not be suppressed in the array region.

In another method, intensity is used as a feature of segmentation to group similar intensity pixels together. Then, the same set of parameters are applied for the same group of pixels (intensity-based). However, this method also has a number of disadvantages. For example, an intensity-based segmentation algorithm can be used when a geometry feature scatters uniformly. Often, however, this is not enough. Therefore, other property-based segmentation is needed.

Accordingly, it would be advantageous to develop methods and systems for detecting defects on a wafer that can achieve better detection of defects by utilizing the knowledge that defects of interest and nuisance/noise reside in different segments geometrically.

SUMMARY OF THE INVENTION

The following description of various embodiments is not to be construed in any way as limiting the subject matter of the appended claims.

One embodiment relates to a computer-implemented method for detecting defects on a wafer. The computer-implemented method includes acquiring raw output for a wafer generated by an inspection system. The computer-implemented method also includes identifying one or more characteristics of the raw output that correspond to one or more geometrical characteristics of patterned features formed on the wafer. In addition, the computer-implemented method includes assigning individual output in the raw output to different segments based on the identified one or more characteristics of the raw output such that the one or more geometrical characteristics of the patterned features that correspond to each of the different segments are different. Furthermore, the computer-implemented method includes separately assigning one or more defect detection parameters to the different segments. The computer-implemented method also includes applying the assigned one or more defect detection parameters to the individual output assigned to the different segments to thereby detect defects on the wafer.

Each of the steps of the computer-implemented method described above may be performed as described further herein. The computer-implemented method described above may include any other step(s) of any other method(s) described herein. The computer-implemented method described above may be performed using any of the systems described herein.

Another embodiment relates to a computer-readable medium that includes program instructions executable on a computer system for performing a method for detecting defects on a wafer. The method includes the steps of the computer-implemented method described above. The computer-readable medium may be further configured as described herein. The steps of the method may be performed as described further herein. In addition, the method for which the program instructions are executable may include any other step(s) of any other method(s) described herein.

An additional embodiment relates to a system configured to detect defects on a wafer. The system includes an inspection subsystem configured to generate raw output for a wafer by scanning the wafer. The system also includes a computer subsystem configured to acquire the raw output. The computer subsystem is also configured to identify one or more characteristics of the raw output that correspond to one or more geometrical characteristics of patterned features formed on the wafer. In addition, the computer subsystem is configured to assign individual output in the raw output to different segments based on the identified one or more characteristics of the raw output such that the one or more geometrical characteristics of the patterned features that correspond to each of the different segments are different. The computer subsystem is further configured to separately assign one or more defect detection parameters to the different segments. Furthermore, the computer subsystem is configured to apply the assigned one or more defect detection parameters to the individual output assigned to the different segments to thereby detect defects on the wafer. The system may be further configured as described herein.

BRIEF DESCRIPTION OF THE DRAWINGS

Other objects and advantages of the invention will become apparent upon reading the following detailed description and upon reference to the accompanying drawings in which.

Figure 1:
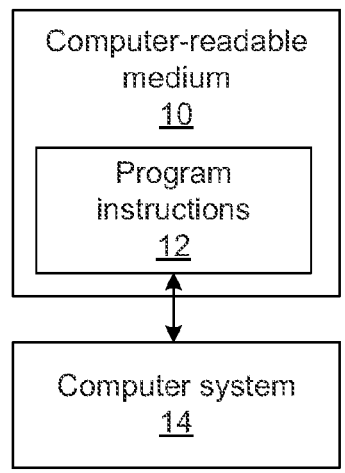
FIG. 1 is a block diagram illustrating one embodiment of a computer-readable medium that includes program instructions executable on a computer system for performing one or more of the method embodiments described herein.

While the invention is susceptible to various modifications and alternative forms, specific embodiments thereof are shown by way of example in the drawings and will herein be described in detail. It should be understood, however, that the drawings and detailed description thereto are not intended to limit the invention to the particular form disclosed, but on the contrary, the intention is to cover all modifications, equivalents and alternatives falling within the spirit and scope of the present invention as defined by the appended claims.

DETAILED DESCRIPTION OF THE PREFERRED EMBODIMENTS

Although embodiments are described herein with respect to wafers, it is to be understood that the embodiments may be used for detecting defects on another specimen such as a reticle, which may also be commonly referred to as a mask or a photomask. Many different types of reticles are known in the art, and the terms "reticle," "mask," and "photomask" as used herein are intended to encompass all types of reticles known in the art.

One embodiment relates to a computer-implemented method for detecting defects on a wafer. The computer-implemented method includes acquiring raw output for a wafer generated by an inspection system. Acquiring the raw output for the wafer may be performed using the inspection system. For example, acquiring the raw output may include using the inspection system to scan light over the wafer and to generate raw output responsive to light scattered and/or reflected from the wafer detected by the inspection system during scanning. In this manner, acquiring the raw output may include scanning the wafer. However, acquiring the raw output does not necessarily include scanning the wafer. For example, acquiring the raw output may include acquiring the raw output from a storage medium in which the raw output has been stored (e.g., by the inspection system). Acquiring the raw output from the storage medium may be performed in any suitable manner, and the storage medium from which the output is acquired may include any of the storage media described herein. In any case, the method includes raw output (e.g., raw data) collection.

In one embodiment, the raw output is responsive to light scattered from the wafer. In particular, the raw output may be responsive to light scattered from the wafer and detected by the inspection system. Alternatively, the raw output may be responsive to light reflected from the wafer and detected by the inspection system. The raw output may include any suitable raw output and may vary depending on the configuration of the inspection system. For example, the raw output may include signals, data, image data, etc. In addition, the raw output may be generally defined as output for at least a portion (e.g., multiple pixels) of the entire output generated for the wafer by the inspection system. Furthermore, the raw output may include all of the raw output generated for the entire wafer by the inspection system, all of the raw output generated for the entire portion of the wafer that is scanned by the inspection system, all of the raw output generated for the wafer by one channel of the inspection system, etc., regardless of whether the raw output corresponds to defects on the wafer.

In contrast, individual output may be generally defined as output for an individual pixel of the entire output generated for the wafer by the inspection system. Therefore, the raw output may include multiple individual output. In other words, the individual output may be output separately generated for different locations on the wafer. For example, the individual output may include individual, discrete output generated for different locations on the wafer. In particular, the different locations may correspond to different "inspection points" on the wafer. In other words, the different locations may correspond to locations on the wafer for which output is separately generated by the inspection system. In this manner, the different locations may correspond to each location on the wafer at which a "measurement" is performed by the inspection system. As such, the different locations may vary depending on the configuration of the inspection system (e.g., the manner in which the inspection system generates output for the wafer). The individual output includes individual output that does and does not correspond to defects on the wafer.

The inspection system may be configured as described herein. For example, the inspection system may be configured for dark field (DF) inspection of the wafer. In this manner, the inspection system may include a DF inspection system. The DF inspection system may be configured as described further herein. In another example, the inspection system may be configured for bright field (BF) inspection of the wafer. In this manner, the inspection system may include a BF inspection system. The BF inspection system may have any suitable configuration known in the art. The inspection system may also be configured for BF and DF inspection. Furthermore, the inspection system may be configured as a scanning electron microscopy (SEM) inspection and review system, and such an inspection system may have any suitable configuration known in the art. In addition, the inspection system may be configured for inspection of patterned wafers and possibly also unpatterned wafers.

The computer-implemented method also includes identifying one or more characteristics of the raw output that correspond to one or more geometrical characteristics of patterned features formed on the wafer. In one embodiment, the identified one or more characteristics of the raw output include projections along lines within the raw output. A projection can be generally defined as a group, cluster, or summation of individual output that has some pattern within the raw output. For example, projections along horizontal and vertical lines of the raw output can be gathered. In this manner, x and y projections within the raw output can be identified that define or correspond to one or more geometrical characteristics of the patterned features. As such, identifying the one or more characteristics of the raw output may include performing two-dimensional (2D) projection of the raw output. However, the one or more characteristics of the raw output that correspond to the one or more geometrical characteristics of patterned features formed on the wafer may include any other characteristic(s) of the raw output. Identifying the one or more characteristics of the raw output as described above may be performed in any suitable manner using any suitable method and/or algorithm.

In one embodiment, the one or more geometrical characteristics of the patterned features include edges, shape, texture, a mathematical calculation that defines geometry of the patterned features, or some combination thereof. For example, characteristics that can be used for geometric-based segmentation, which may be performed as described further herein, include edges, shape, texture, any mathematical calculation/transformation that defines the geometry, or some combination thereof. Although all patterned features formed on a wafer may have some roughness and therefore some "texture," texture is different than roughness in that roughness is generally used to refer to and describe roughness just on the periphery of patterned features white texture generally refers to the overall texture (e.g., as designed or not) of patterned features. One example of a mathematical calculation/transformation that can be used to define the geometry of the patterned features is a Fourier filtering algorithm, which can be used to describe a relationship between geometry and light scattering. For example, a Fourier filtering algorithm can be used to predict projections in the raw output that will correspond to one or more geometrical characteristics of the patterned features.

In one embodiment, identifying the one or more characteristics of the raw output is performed based on how a design layout of the patterned features will affect the one or more characteristics of the raw output. For example, a characteristic that can be used for segmentation, which can be performed as described herein, is the design layout. In particular, the design layout can be used to identify one or more geometrical characteristics of patterned features in the design layout. One or more characteristics (e.g., projections) of the raw output that correspond to the one or more identified geometrical characteristics can then be determined (e.g., empirically, theoretically, etc.). In this manner, one or more expected characteristics of the raw output that will correspond to one or more geometrical characteristics of the patterned features can be determined. Those one or more expected characteristics can then be compared to one or more characteristics of the raw output in any suitable manner to identify the one or more characteristics of the raw output that correspond to one or more geometrical characteristics of the patterned features. The design layout used in this step may be acquired in any suitable manner and may have any suitable format.

In another embodiment, identifying the one or more characteristics of the raw output is performed while acquiring the raw output is being performed. In this manner, identifying the one or more characteristics of the raw output may be performed on-the-fly as the wafer is being scanned by the inspection system. For example, identifying the one or more characteristics of the raw output can be performed using reference raw output for the wafer that will be compared to the raw output to detect defects on the wafer and that is acquired for the wafer in the same scan as the raw output. The reference raw output may include any of the references described herein. As such, other steps described herein (e.g., segmentation) that are performed using the one or more identified characteristics of the raw output may also be performed on-the-fly during acquisition of the raw output for the wafer.

The computer-implemented method also includes assigning individual output in the raw output to different segments based on the identified one or more characteristics of the raw output such that the one or more geometrical characteristics of the patterned features that correspond to each of the different segments are different. In this manner, the embodiments described herein are configured for geometry-based segmentation. More specifically, the embodiments described herein utilize how the geometrical characteristic(s) (e.g., shape) of wafer patterns will affect the raw output and separate the patterns that affect the raw output differently into different segments. In other words, the embodiments described herein utilize how the geometrical characteristic(s) (e.g., shape) of patterns on the wafer will affect the raw output to separate individual output in the raw output into different segments. For instance, patterned features that have one or more different geometrical characteristics may have different effects on light scattered from the wafer and thereby may have different effects on the raw output generated for the wafer. Those patterned features can be effectively separated into different segments by the embodiments described herein. Assigning the individual output in the raw output to different segments as described herein can be performed in any suitable manner using any suitable method and/or algorithm.

"Segments" can be generally defined as different portions of an entire range of possible values for the individual output. The segments may be defined based on values for different characteristics of the individual output depending on the defect detection algorithm that uses the segments. For instance, in the multiple die auto-thresholding (MDAT) algorithm, the value for the characteristic of the individual output that is used to define the segments may include median intensity value. In one such illustrative and non-limiting example, if the entire range of median intensity values is from 0 to 255, a first segment may include median intensity values from 0 to 100 and a second segment may include median intensity values from 101 to 255. In this manner, the first segment corresponds to darker areas in the raw output, and the second segment corresponds to brighter areas in the raw output. In some instances, the segments can be defined using one wafer, and for wafers having similar geometry as that one wafer, the predefined segments can be used.

In one embodiment, identifying the one or more characteristics of the raw output and assigning the individual output to the different segments is performed automatically without user input. For example, the embodiments described herein can utilize the geometrical characteristic(s) (e.g., shape) of patterns on the wafer and projection to automatically separate the individual output in the raw output into different segments. In this manner, unlike methods that include manually setting up regions of interest (ROI) and applying the same set of parameters for defect detection in the same ROI, as design rules shrink and as the different areas on the wafer to be segmented get smaller, segmentation will not become more complicated using the embodiments described herein. In addition, unlike manual methods, automatically identifying the one or more characteristics of the raw output and assigning the individual output to the different segments without user input is not affected by inspection system stage accuracy and resolution limitations. Therefore, using the embodiments described herein for segmentation, the inspection system stage accuracy and resolution limitations will not make segmentation impossible.

In another embodiment, assigning the individual output to the different segments is performed without regard to design data associated with the patterned features. For example, although the design layout may be used as described above to determine one or more expected characteristics of the raw output that will correspond to one or more geometrical characteristics of the patterned features, segmentation is not performed based on the design data itself. In other words, segmentation is based on how the one or more geometrical characteristics of the patterned features will affect the raw output, but is not based on the one or more geometrical characteristics of the patterned features themselves. In this manner, unlike other methods and systems that segment raw output based on the design data associated with patterned features, performing segmentation based on how the one or more geometrical characteristics of the patterned features will affect the raw output may result in patterned features associated with different design data, different electrical functions, different electrical characteristics, different criticalities to the performance of the device being formed using the patterned features, etc. being assigned to the same segment if those patterned features will affect the raw output in the same manner. For example, performing segmentation based on how the geometrical characteristic(s) will affect characteristic(s) (e.g., intensity) of the raw output instead of the geometry itself may result in patterned features that produce significant noise in the raw output being assigned to the same segment regardless of the design data associated with those pattern features and other patterned features that produce negligible noise in the raw output being assigned to a different segment again regardless of the design data associated with those other patterned features. In this manner, high noise patterned features can be segmented together, and low noise patterned features can be segmented together.

In an additional embodiment, assigning the individual output to the different segments is performed without regard to intensity of the individual output. In other words, although the segmentation is performed based on the one or more identified characteristics of the raw output, which may be identified based on intensity of multiple individual output in the raw output, the segmentation is not performed based on intensity of the individual output itself. For example, projections along lines within the raw output may include individual output that have a variety and possibly dramatically different intensities. Nevertheless, all of that individual output may correspond to the same one or more geometrical characteristics of patterned features such as page breaks. As such, all of the individual output that corresponds to the same one or more geometrical characteristics of the patterned features can be assigned to the same segment even though all of that individual output may have dramatically different intensities. In this manner, unlike methods for performing segmentation based on the intensity of individual pixels, the segmentation performed by the embodiments described herein will not be affected by non-uniform scattering from the patterned features.

In some embodiments, assigning the individual output to the different segments includes analyzing the identified one or more characteristics of the raw output and applying thresholds to the individual output. For example, as described above, projections along horizontal and vertical lines in the raw output can be gathered. The projections can then be analyzed, and thresholds can be set to separate the individual output in the raw output into different areas of interest (segments). Analyzing the identified one or more characteristics of the raw output and applying thresholds to the individual output may reduce the number of individual output corresponding to boundary regions from being inappropriately assigned to the segments.

In one embodiment, the one or more geometrical characteristics that correspond to one of the different segments include one or more geometrical characteristics of page breaks, and the one or more geometrical characteristics that correspond to another of the different segments include one or more geometrical characteristics of array areas. Page breaks are generally defined in the art as regions of a die separating substantially continuous regions of physical memory. Each of the continuous regions of physical memory may be commonly referred to as a page frame. Performing segmentation as described herein, one or more characteristics of the raw output (e.g., the x and/or y projections) that define the geometry for page breaks in array regions can be identified and used to assign individual output corresponding to the page breaks to one segment and to assign individual output corresponding to array regions to a different segment.

In another embodiment, the one or more characteristics of the raw output that correspond to the one or more geometrical characteristics of some of the patterned features cannot be suppressed by Fourier filtering. For example, unlike some methods for segmentation, even if the distance between page breaks is larger than Fourier filtering can perform, the page break can be suppressed in the array region. In one such example, for some inspection systems, if the width of a page break is about 5 µm and the spacing between page breaks is about 5 µm, Fourier filtering becomes impractical if not impossible while manual set up of ROI also becomes impractical if not impossible. Therefore, the signal (noise) produced in the raw output by the page breaks may not be suppressed and can thereby reduce the defect detection sensitivity that can be achieved using the raw output. However, using the embodiments described herein, the individual output that corresponds to the page breaks can be identified (e.g., based on projections within the raw output), and the individual output that corresponds to the page breaks can be assigned to one segment while other individual output can be assigned to other segments such that as described further herein different sensitivities can be used to detect defects in different segments.

The computer-implemented method further includes separately assigning one or more defect detection parameters to the different segments. One or more defect detection parameters can be separately assigned to all of the different segments. Therefore, some of the individual output may not be ignored when it comes to defect detection. Instead, defects can be detected using the individual output assigned to all of the different segments. In other words, defects can be detected using all segments of the raw output. In this manner, different segments can be treated differently with different inspection recipes. The different inspection recipes may be different in the defect detection algorithms that are assigned to the different segments. Alternatively, the different inspection recipes may be different in one or more parameters of the same defect detection algorithm that are assigned to the different segments. The defect detection algorithms that are assigned to the different segments or one or more parameters of which are assigned to the different segments may include any suitable detect detection algorithms. For example, the defect detection algorithm may be a segmented auto-thresholding (SAT) algorithm or a MDAT algorithm. Such defect detection algorithms may be particularly suitable for BF inspection. However, the defect detection algorithm may be a defect detection algorithm that is suitable for DF inspection. For example, the defect detection algorithm may be a FAST algorithm or an HLAT algorithm.

The different inspection recipes may also be different in one or more optical parameters of the inspection system that are used to acquire the raw output for the wafer. For example, in a multi-pass inspection, different passes may be performed with different values for at least one optical parameter (e.g., polarization, wavelength, angle of illumination, angle of collection, etc.) of the inspection system, and raw output generated in the different passes may be used to detect defects in different regions of the wafer in which patterned features having one or more different geometrical characteristics are formed. In this manner, regions of the wafer that include patterned features having one or more different geometrical characteristics can be inspected using raw output generated in different passes of a multi-pass inspection performed using one or more different optical parameters.

In one embodiment, the one or more defect detection parameters include a threshold to be applied to a difference between the individual output and a reference. In this manner, different thresholds can be applied to the difference between the individual output and the reference depending on the segment to which the individual output has been assigned. For example, a reference such as an 8-bit reference image) may be subtracted from the individual output in the raw output (such as an 8-bit test image) regardless of the segment to which the individual output has been assigned. The reference may include any suitable reference such as individual output corresponding to a die on the wafer that is different than the die in which the individual output, from which the reference is being subtracted, has been generated, a cell on the wafer that is different than the cell in which the individual output, from which the reference is being subtracted, has been generated, etc. Any individual output having a difference above the assigned threshold may be identified as a defect. In this manner, defects can be detected with different thresholds depending on the segment to which the individual output has been assigned.

In another embodiment, separately assigning the one or more defect detection parameters to the different segments is performed such that defects are detected using the individual output assigned to the different segments with different sensitivities. Therefore, the embodiments described herein can achieve better detection of defects by utilizing the knowledge that defects of interest (DOI) and nuisance/noise reside in different segments geometrically. For example, different geometries can exhibit different types of defects. In one such example, in an array pattern region, the raw output may include alternating line-like patterns of relatively bright individual output and relatively dark individual output. In some such instances, DOI may be located in portions of the raw output that include the relatively bright individual output while nuisance defects may be located in portions of the raw output that include the relatively dark individual output. In this manner, with segmentation using characteristic(s) that define the geometry (e.g., the x or y projection for page break in the array region), the sensitivity of a detection algorithm can be set up differently for better sensitivity in the array area and less nuisance from the page break. Therefore, the embodiments described herein advantageously allow an automatic way of separating different geometric patterns of the wafer into different segments. This segmentation makes it possible for these areas to be treated differently and better sensitivity can be achieved. Different geometries also scatter light differently. In this manner, some geometries may cause the raw output to be relatively noisy while other geometries may cause the raw output to be relatively quiet. However, using only intensity of the individual output for segmentation, individual output corresponding to relatively noisy and relatively quiet regions in the raw output can be grouped together (e.g., due to poorly defined boundaries). In contrast, in the embodiments described herein, for defects that are located in areas of the wafer that have one or more geometrical characteristics that correspond to less noise in the raw output, higher sensitivity can be achieved. In addition, for narrow band inspection systems, defects can often be buried in noise since patterns also scatter a significant amount of light. However, the embodiments described herein make it possible to detect those defects that are detuned by noise from nearby patterns.

The computer-implemented method further includes applying the assigned one or more defect detection parameters to the individual output assigned to the different segments to thereby detect defects on the wafer. As described above, different segments can be treated differently with different inspection recipes. In this manner, applying the assigned one or more defect detection parameters to the individual output may include inspecting segments with different recipes to thereby detect defects on the wafer. For example, the segment to which the individual output has been assigned can be used to determine the threshold that is to be applied to the difference between the individual output and the reference. After determining the segment to which the individual output has been assigned and assigning the one or more defect detection parameters to the different segments, the assigned one or more defect detection parameters can be applied to the individual output assigned to the different segments as would normally be performed.

In one embodiment, acquiring the raw output is performed in one pass of a multi-pass inspection of the wafer, and the computer-implemented method is not performed for raw output acquired in another pass of the multi-pass inspection. In this manner, segmentation as described herein may be performed for only one pass of a multi-pass inspection. Raw output acquired in other passes can be used for other purposes. For example, multi-pass inspection may serve the segmentation purpose with one pass having the optimum signal to defects and another pass providing the geometry-based segmentation. In particular, different passes of the multi-pass inspection may be performed with one or more different defect detection parameters and/or one or more different optical parameters such that the raw output and/or the defect detection results are different for different passes. In one such example, one optical mode used in one pass of the multi-pass inspection may allow segmentation while another optical mode of the inspection system used in another pass of the multi-pass inspection may provide the highest sensitivity to DOI.

In another embodiment, additional defects are detected using the raw output acquired in the other pass, and the method includes combining the defects and the additional defects to generate inspection results for the wafer. For example, as described above, one pass of a multi-pass inspection may be used for segmentation while another pass of the multi-pass inspection may be used to detect DOI with optimum signal. Therefore, different passes of the multi-pass inspection may detect different types of defects. In this manner, the results of the different passes of the multi-pass inspection can be combined to generate the overall inspection results for the wafer. The results of the defects detected using the raw output acquired in different passes may be combined after defect detection using the raw output generated in all of the different passes has been performed. Alternatively, the defect detection results generated using the raw output acquired in different passes may be combined on-the-fly or while some of the raw output is still being acquired.

In an additional embodiment, the method includes applying one or more predetermined defect detection parameters to the raw output to detect additional defects on the wafer and combining the defects and the additional defects to generate inspection results for the wafer. For example, a reference (such as an 8-bit reference image) may be subtracted from the individual output in the raw output (such as an 8-bit test image) regardless of the segment to which the individual output has been assigned. The reference may include any suitable reference such as those described above. In addition, the same reference can be used for detecting defects by applying the assigned one or more defect detection parameters to the individual output and by applying one or more predetermined defect detection parameters to the raw output. The result of the subtraction may be an absolute difference. A predetermined, direct difference threshold may then be applied to the absolute difference, and any individual output having an absolute difference above the threshold may be identified as a defect. In addition, the same predetermined, direct difference threshold may be applied to the absolute difference regardless of the segment to which the individual output has been assigned. Defects detected in this manner may then be combined with defects detected by applying the assigned one or more defect detection parameters to the individual output to generate the final inspection results for the wafer. For example, a defective mask may be separately generated for all defects detected in any manner. Region "grow" may be performed from both difference images, and a final mask for all defects may be generated.

Detecting defects in different manners as described above may provide defect redetection, which may be advantageous for a number of reasons. For example, automatic 2D projection and geometry-based segmentation provide robust defect redetection and ease of use for detect redetection. In addition, the segmentation described herein provides a dynamic way of mapping defect and reference images. For example, if the segment is noisy, the difference can be detuned. In contrast, if the segment is cleaner, the difference can be enlarged. In addition, double detection as described above lowers the possibility of false alarms from either detection method.

The method may also include storing results of any of the step(s) of the method in a storage medium. The results may include any of the results described herein and may be stored in any manner known in the art. For example, the segments to which the individual output is assigned and/or the one or more defect detection parameters assigned to the different segments may be used to generate a data structure such as a look up table that is stored on a storage medium coupled to the inspection system. The storage medium may include any suitable storage medium known in the art. After the results have been stored, the results can be accessed in the storage medium and used as described herein, formatted for display to a user, used by another software module, method, or system, etc. Furthermore, the results may be stored "permanently," "semi-permanently," temporarily, or for some period of time. For example, the storage medium may be random access memory (RAM), and the results may not necessarily persist indefinitely in the storage medium. Storing the results may also be performed as described in commonly owned U.S. patent application Ser. No. 12/234,201 by Bhaskar et al. filed Sep. 19, 2008, which published as U.S. Patent Application Publication No. 2009/0080759 on Mar. 26, 2009, and which is incorporated by reference as if fully set forth herein.

Turning now to the drawings, it is noted that the figures are not drawn to scale. In particular, the scale of some of the elements of the figures is greatly exaggerated to emphasize characteristics of the elements. It is also noted that the figures are not drawn to the same scale. Elements shown in more than one figure that may be similarly configured have been indicated using the same reference numerals.

Another embodiment relates to a computer-readable medium that includes program instructions executable on a computer system for performing a method (i.e., a computer-implemented method) for detecting defects on a wafer. One such embodiment is shown in FIG. 1. For example, as shown in FIG. 1, computer-readable medium 10 includes program instructions 12 executable on computer system 14 for performing the method for detecting defects on a wafer described above. The computer-implemented method for which the program instructions are executable may include any other step(s) of any other method(s) described herein.

Program instructions 12 implementing methods such as those described herein may be stored on computer-readable medium 10. The computer-readable medium may be a storage medium such as a read-only memory, a RAM, a magnetic or optical disk, or a magnetic tape or any other suitable computer-readable medium known in the art.

The program instructions may be implemented in any of various ways, including procedure-based techniques, component-based techniques, and/or object-oriented techniques, among others. For example, the program instructions may be implemented using Matlab, Visual Basic, ActiveX controls, C, C++ objects, C#, JavaBeans, Microsoft Foundation Classes ("MFC"), or other technologies or methodologies, as desired.

Computer system 14 may take various forms, including a personal computer system, mainframe computer system, workstation, system computer, image computer, programmable image computer, parallel processor, or any other device known in the art. In general, the term "computer system" may be broadly defined to encompass any device having one or more processors, which executes instructions from a memory medium.

Figure 2:
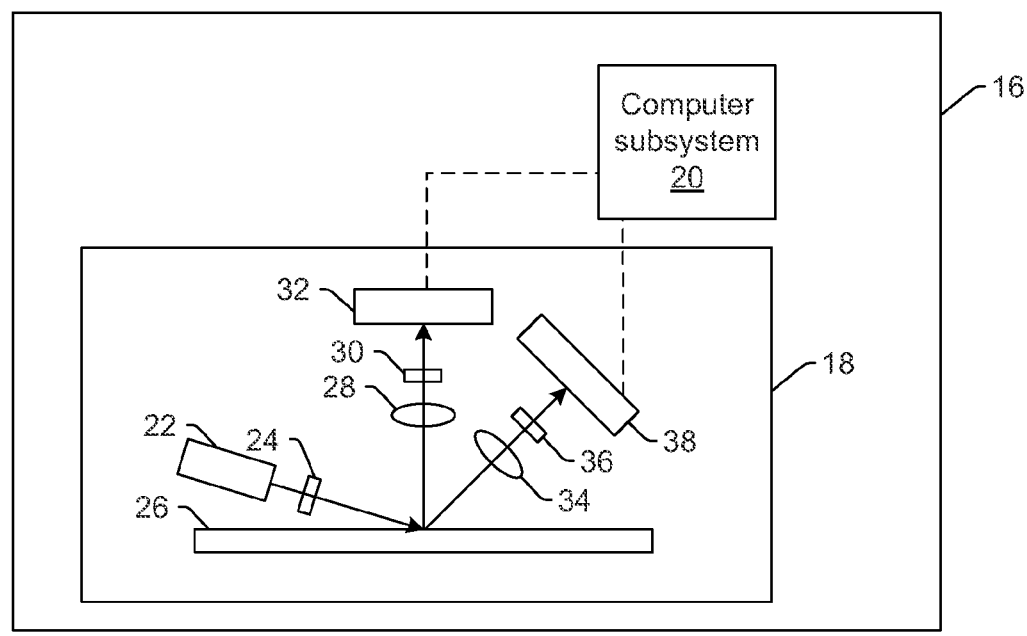
FIG. 2 is a schematic diagram illustrating a side view of one embodiment of a system configured to detect defects on a wafer.

An additional embodiment relates to a system configured to detect defects on a wafer. One embodiment of such a system is shown in FIG. 2. As shown in FIG. 2, system 16 includes inspection subsystem 18 and computer subsystem 20. The inspection subsystem is configured to generate raw output for a wafer by scanning the wafer. For example, as shown in FIG. 2, the inspection subsystem includes light source 22 such as a laser. Light source 22 is configured to direct light to polarizing component 24. In addition, the inspection subsystem may include more than one polarizing component (not shown), each of which may be positioned independently in the path of the light from the light source. Each of the polarizing components may be configured to alter the polarization of the light from the light source in a different manner. The inspection subsystem may be configured to move the polarizing components into and out of the path of the light from the light source in any suitable manner depending on which polarization setting is selected for illumination of the wafer during a scan. The polarization setting used for the illumination of the wafer during a scan may include p-polarized (P), s-polarized (S), or circularly polarized (C).

Light exiting polarizing component 24 is directed to wafer 26 at an oblique angle of incidence, which may include any suitable oblique angle of incidence. The inspection subsystem may also include one or more optical components (not shown) that are configured to direct light from tight source 22 to polarizing component 24 or from polarizing component 24 to wafer 26. The optical components may include any suitable optical components known in the art such as, but not limited to, a reflective optical component. In addition, the tight source, the polarizing component, and/or the one or more optical components may be configured to direct the light to the wafer at one or more angles of incidence (e.g., an oblique angle of incidence and/or a substantially normal angle of incidence). The inspection subsystem may be configured to perform the scanning by scanning the tight over the wafer in any suitable manner.

Light scattered from wafer 26 may be collected and detected by multiple channels of the inspection subsystem during scanning. For example, light scattered from wafer 26 at angles relatively close to normal may be collected by lens 28. Lens 28 may include a refractive optical element as shown in FIG. 2. In addition, lens 28 may include one or more refractive optical elements and/or one or more reflective optical elements. Light collected by lens 28 may be directed to polarizing component 30, which may include any suitable polarizing component known in the art. In addition, the inspection subsystem may include more than one polarizing component (not shown), each of which may be positioned independently in the path of the tight collected by the lens. Each of the polarizing components my be configured to alter the polarization of the light collected by the lens in a different manner. The inspection subsystem may be configured to move the polarizing components into and out of the path of the light collected by the lens in any suitable manner depending on which polarization setting is selected for detection of the light collected by lens 28 during scanning. The polarization setting used for the detection of the light collected by lens 28 during scanning may include any of the polarization settings described herein (e.g., P, S, and unpolarized (N)).

Light exiting polarizing component 30 is directed to detector 32. Detector 32 may include any suitable detector known in the art such as a charge coupled device (CCD) or another type of imaging detector. Detector 32 is configured to generate raw output that is responsive to the scattered light collected by lens 28 and transmitted by polarizing component 30 if positioned in the path of the collected scattered light. Therefore, lens 28, polarizing component 30 if positioned in the path of the light collected by lens 28, and detector 32 form one channel of the inspection subsystem. This channel of the inspection subsystem may include any other suitable optical components (not shown) known in the art such as a Fourier filtering component.

Light scattered from wafer 26 at different angles may be collected by lens 34. Lens 34 may be configured as described above. Light collected by lens 34 may be directed to polarizing component 36, which may include any suitable polarizing component known in the art. In addition, the inspection subsystem may include more than one polarizing component (not shown), each of which may be positioned independently in the path of the light collected by the lens. Each of the polarizing components may be configured to alter the polarization of the light collected by the lens in a different manner. The inspection subsystem may be configured to move the polarizing components into and out of the path of the light collected by the lens in any suitable manner depending on which polarization setting is selected for detection of the light collected by lens 34 during scanning. The polarization setting used for detection of the light collected by lens 34 during scanning may include P, S, or N.

Light exiting polarizing component 36 is directed to detector 38, which may be configured as described above. Detector 38 is also configured to generate raw output that is responsive to the collected scattered light that passes through polarizing component 36 if positioned in the path of the scattered light. Therefore, lens 34, polarizing component 36 if positioned in the path of the light collected by lens 34, and detector 38 may form another channel of the inspection subsystem. This channel may also include any other optical components (not shown) described above. In some embodiments, lens 34 may be configured to collect light scattered from the wafer at polar angles from about 20 degrees to about 70 degrees. In addition, lens 34 may be configured as a reflective optical component (not shown) that is configured to collect light scattered from the wafer at azimuthal angles of about 360 degrees.

The inspection subsystem shown in FIG. 2 may also include one or more other channels (not shown). For example, the inspection subsystem may include an additional channel, which may include any of the optical components described herein such as a lens, one or more polarizing components, and a detector, configured as a side channel. The lens, the one or more polarizing components, and the detector may be further configured as described herein. In one such example, the side channel may be configured to collect and detect light that is scattered out of the plane of incidence (e.g., the side channel may include a lens, which is centered in a plane that is substantially perpendicular to the plane of incidence, and a detector configured to detect light collected by the lens).

If inspection of the wafer includes more than one pass, the values of any optical parameter(s) of the inspection subsystem may be altered in any suitable manner if necessary between passes. For example, to change the illumination polarization states between passes, polarizing component 24 may be removed and/or replaced as described herein with a different polarizing component. In another example, to change illumination angles between passes, the position of the light source and/or any other optical components (e.g., polarizing component 24) used to direct the tight to the wafer may be altered between passes in any suitable manner.

Computer subsystem 20 is configured to acquire the raw output generated by the inspection subsystem. For example, raw output generated by the detectors during scanning may be provided to computer subsystem 20. In particular, the computer subsystem may be coupled to each of the detectors (e.g., by one or more transmission media shown by the dashed lines in FIG. 2, which may include any suitable transmission media known in the art) such that the computer subsystem may receive the raw output generated by the detectors. The computer subsystem may be coupled to each of the detectors in any suitable manner. The raw output generated by the detectors during scanning of the wafer may include any of the raw output described herein.

The computer subsystem is configured to identify one or more characteristics of the raw output that correspond to one or more geometrical characteristics of patterned features formed on the wafer according to any of the embodiments described herein. The one or more characteristics of the raw output may include any such characteristics described herein. The one or more geometrical characteristics may also include any such characteristics described herein. The patterned features may include any of the patterned features described herein.

In addition, the computer subsystem is configured to assign individual output in the raw output to different segments based on the identified one or more characteristics of the raw output such that the one or more geometrical characteristics of the patterned features that correspond to each of the different segments are different. The computer subsystem may be configured to assign the individual output to the different segments according to any of the embodiments described herein. The individual output may include any of the individual output described herein. The different segments may be configured as described herein. The identified one or more characteristics of the raw output may include any such characteristics described herein.

The computer subsystem is further configured to separately assign one or more defect detection parameters to the different segments according to any of the embodiments described herein. The one or more defect detection parameters may include any of the defect detection parameters described herein. The computer subsystem is also configured to apply the assigned one or more defect detection parameters to the individual output assigned to the different segments to thereby detect defects on the wafer, which may be performed according to any of the embodiments described herein. The assigned one or more defect detection parameters may include any such parameters described herein.

The computer subsystem may be configured to perform any other step(s) of any method embodiment(s) described herein. The computer subsystem, the inspection subsystem, and the system may be further configured as described herein.

It is noted that FIG. 2 is provided herein to generally illustrate one configuration of an inspection subsystem that may be included in the system embodiments described herein. Obviously, the inspection subsystem configuration described herein may be altered to optimize the performance of the inspection subsystem as is normally performed when designing a commercial inspection system. In addition, the systems described herein may be implemented using an existing inspection system (e.g., by adding functionality described herein to an existing inspection system) such as the Puma 90xx, 91xx, and 93xx series of tools that are commercially available from KLA-Tencor, Milpitas, Calif. For some such systems, the methods described herein may be provided as optional functionality of the system (e.g., in addition to other functionality of the system). Alternatively, the system described herein may be designed "from scratch" to provide a completely new system.

Further modifications and alternative embodiments of various aspects of the invention will be apparent to those skilled in the art in view of this description. For example, methods and systems for detecting defects on a wafer are provided. Accordingly, this description is to be construed as illustrative only and is for the purpose of teaching those skilled in the art the general manner of carrying out the invention. It is to be understood that the forms of the invention shown and described herein are to be taken as the presently preferred embodiments. Elements and materials may be substituted for those illustrated and described herein, parts and processes may be reversed, and certain features of the invention may be utilized independently, all as would be apparent to one skilled in the art after having the benefit of this description of the invention. Changes may be made in the elements described herein without departing from the spirit and scope of the invention as described in the following claims.

What is claimed is:

1. A computer-implemented method for detecting defects on a wafer, comprising:
   acquiring raw output for a wafer generated by an inspection system;
   identifying one or more characteristics of the raw output that correspond to one or more geometrical characteristics of patterned features formed on the wafer;
   assigning individual output in the raw output to different segments based on the identified one or more characteristics of the raw output such that the one or more geometrical characteristics of the patterned features that correspond to each of the different segments are different, wherein the one or more geometrical characteristics that correspond to one of the different segments comprise one or more geometrical characteristics of page breaks, and wherein the one or more geometrical characteristics that correspond to another of the different segments comprise one or more geometrical characteristics of array areas;
   separately assigning one or more defect detection parameters to the different segments; and
   applying the assigned one or more defect detection parameters to the individual output assigned to the different segments to thereby detect defects on the wafer.

2. The method of claim 1, wherein the raw output is responsive to light scattered from the wafer.

3. The method of claim 1, wherein the identified one or more characteristics of the raw output comprise projections along lines within the raw output.

4. The method of claim 1, wherein the one or more geometrical characteristics of the patterned features comprise edges, shape, texture, a mathematical calculation that defines geometry of the patterned features, or some combination thereof.

5. The method of claim 1, wherein said identifying is performed based on how a design layout of the patterned features will affect the one or more characteristics of the raw output.

6. The method of claim 1, wherein said identifying is performed while said acquiring is being performed.

7. The method of claim 1, wherein said identifying and said assigning the individual output are performed automatically without user input.

8. The method of claim 1, wherein said assigning the individual output is performed without regard to design data associated with the patterned features.

9. The method of claim 1, wherein said assigning the individual output is performed without regard to intensity of the individual output.

10. The method of claim 1, wherein said assigning the individual output comprises analyzing the identified one or more characteristics of the raw output and applying thresholds to the individual output.

11. The method of claim 1, wherein the one or more characteristics of the raw output that correspond to the one or more geometrical characteristics of some of the patterned features cannot be suppressed by Fourier filtering.

12. The method of claim 1, wherein the one or more defect detection parameters comprise a threshold to be applied to a difference between the individual output and a reference.

13. The method of claim 1, wherein said separately assigning the one or more defect detection parameters is performed such that defects are detected using the individual output assigned to the different segments with different sensitivities.

14. The method of claim 1, wherein said acquiring is performed in one pass of a multi-pass inspection of the wafer, and wherein the computer-implemented method is not performed for raw output acquired in another pass of the multi-pass inspection.

15. The method of claim 1, wherein said acquiring is performed in one pass of a multi-pass inspection of the wafer, wherein the computer-implemented method is not performed for raw output acquired in another pass of the multi-pass inspection, wherein additional defects are detected using the raw output acquired in the other pass, and wherein the method further comprises combining the defects and the additional defects to generate inspection results for the wafer.

16. The method of claim 1, further comprising applying one or more predetermined defect detection parameters to the raw output to detect additional defects on the wafer and combining the defects and the additional defects to generate inspection results for the wafer.

17. A computer-readable medium, comprising program instructions executable on a computer system for performing a method for detecting defects on a wafer, wherein the method comprises:
   acquiring raw output for a wafer generated by an inspection system;
   identifying one or more characteristics of the raw output that correspond to one or more geometrical characteristics of patterned features formed on the wafer;
   assigning individual output in the raw output to different segments based on the identified one or more characteristics of the raw output such that the one or more geometrical characteristics of the patterned features that correspond to each of the different segments are different, wherein the one or more geometrical characteristics that correspond to one of the different segments comprise one or more geometrical characteristics of page breaks, and wherein the one or more geometrical characteristics that correspond to another of the different segments comprise one or more geometrical characteristics of array areas;

separately assigning one or more defect detection parameters to the different segments; and applying the assigned one or more defect detection parameters to the individual output assigned to the different segments to thereby detect defects on the wafer.

18. A system configured to detect defects on a wafer, comprising:

an inspection subsystem configured to generate raw output for a wafer by scanning the wafer; and a computer subsystem configured to:

acquire the raw output;

identify one or more characteristics of the raw output that correspond to one or more geometrical characteristics of patterned features formed on the wafer;

assign individual output in the raw output to different segments based on the identified one or more characteristics of the raw output such that the one or more geometrical characteristics of the patterned features that correspond to each of the different segments are different, wherein the one or more geometrical characteristics that correspond to one of the different segments comprise one or more geometrical characteristics of page breaks, and wherein the one or more geometrical characteristics that correspond to another of the different segments comprise one or more geometrical characteristics of array areas;

separately assign one or more defect detection parameters to the different segments; and apply the assigned one or more defect detection parameters to the individual output assigned to the different segments to thereby detect defects on the wafer.

\* \* \* \* \*